US008697103B2

(12) United States Patent
Veeger et al.

(10) Patent No.: US 8,697,103 B2
(45) Date of Patent: *Apr. 15, 2014

(54) ALCOHOLIC PUMP FOAM

(75) Inventors: Marcel Veeger, Goch (DE); Markus Himming, Oberhausen (DE)

(73) Assignee: Deb IP Limited, Denby, Derbyshire (GB)

( * ) Notice: Subject to any disclaimer, the term of this patent is extended or adjusted under 35 U.S.C. 154(b) by 102 days.

This patent is subject to a terminal disclaimer.

(21) Appl. No.: 13/366,787

(22) Filed: Feb. 6, 2012

(65) Prior Publication Data

US 2012/0136069 A1 May 31, 2012

Related U.S. Application Data

(63) Continuation of application No. 12/624,073, filed on Nov. 23, 2009, now Pat. No. 8,124,115, which is a continuation of application No. 11/312,559, filed on Dec. 21, 2005, now Pat. No. 7,670,615.

(30) Foreign Application Priority Data

Dec. 21, 2004 (DE) .................. 10 2004 062 775

(51) Int. Cl.
*A01N 25/00* (2006.01)
*A01N 31/00* (2006.01)
*A01N 31/14* (2006.01)
*A01N 43/04* (2006.01)
*A01N 55/00* (2006.01)
*C11D 3/22* (2006.01)
*C11D 3/37* (2006.01)

(52) U.S. Cl.
USPC .............. 424/405; 514/25; 514/63; 514/715; 514/724; 514/738; 514/781; 510/473; 510/475

(58) Field of Classification Search
USPC .............. 424/405; 514/25, 63, 715, 724, 738, 514/781; 510/473, 475
See application file for complete search history.

(56) References Cited

U.S. PATENT DOCUMENTS

| 3,709,437 A | 1/1973 | Wright |
| 3,963,507 A | 6/1976 | Kuramoto et al. |
| 4,225,456 A | 9/1980 | Schmidt et al. |
| 4,440,653 A | 4/1984 | Briscoe et al. |
| 4,511,486 A | 4/1985 | Shah |
| 4,714,568 A | 12/1987 | Hurnik et al. |
| 5,145,977 A | 9/1992 | Petroff et al. |
| 5,167,950 A | 12/1992 | Lins |
| 5,439,682 A | 8/1995 | Wivell et al. |
| 5,629,006 A | 5/1997 | Hoang et al. |
| 5,843,881 A | 12/1998 | Dubois et al. |
| 5,902,778 A | 5/1999 | Hartmann et al. |
| 5,951,993 A | 9/1999 | Scholz et al. |
| 6,383,997 B1 | 5/2002 | McManus |
| 7,199,090 B2 | 4/2007 | Koivisto et al. |
| 7,597,898 B2 | 10/2009 | Birkel et al. |
| 7,670,615 B2 | 3/2010 | Veeger et al. |
| 7,683,018 B2 | 3/2010 | Koivisto et al. |
| 7,850,048 B2 | 12/2010 | Arminak |
| 8,124,115 B2 * | 2/2012 | Veeger et al. .................. 424/405 |
| 2002/0106399 A1 | 8/2002 | Durden |
| 2002/0127253 A1 | 9/2002 | Scholz et al. |
| 2003/0152644 A1 | 8/2003 | Modak et al. |
| 2004/0167195 A1 | 8/2004 | Muller |
| 2004/0191274 A1 | 9/2004 | Grayson et al. |
| 2005/0031847 A1 | 2/2005 | Martens et al. |
| 2007/0027055 A1 | 2/2007 | Koivisto et al. |
| 2007/0065383 A1 | 3/2007 | Fernandez de Castro et al. |
| 2007/0179207 A1 | 8/2007 | Fernandez de Castro et al. |
| 2007/0258911 A1 | 11/2007 | Fernandez de Castro et al. |
| 2008/0178899 A1 | 7/2008 | Moenks et al. |
| 2010/0160453 A1 | 6/2010 | Koivisto et al. |
| 2011/0201693 A1 | 8/2011 | Littau |
| 2011/0319364 A1 | 12/2011 | Wegner et al. |

FOREIGN PATENT DOCUMENTS

| EP | 0 117 889 | 11/1987 |
| WO | 8501876 A1 | 5/1985 |
| WO | 00 57735 | 10/2000 |

OTHER PUBLICATIONS

Sanders, Paul A.; Aqueous Alcohol Aerosol Foams; Drug and Cosmetic Industry; Aug. 1966 pp. 56-61 and 142-153; vol. 99,, No. 2; Paul W. Alexander, Publisher; New York, New York.
Notice of Reasons for Rejection for Canadian Patent Application No. 2,589,502 mailed Feb. 17, 2012.
Notice of Reasons for Rejection for Japanese Patent Application No. 2008-5000017 mailed Jan. 17, 2012.
Mason Chemical Company brochure for Masurf FS-115/FS-130 100504.
Decision in the Opposition to European Patent No. 1 811 013 B1 (including Auxiliary Requests) dated Apr. 10, 2012.
Notice of Reasons for Rejection for Japanese Patent Application No. 2008-5000017 mailed May 31, 2011.
Gojo submission of Feb. 15, 2012 in the Opposition to European Patent No. 1 811 013 B1 (including Auxiliary Claim sets).
Declaration of Evan Hillman and Annexes submitted in the Opposition to European Patent No. 1 811 013 B1.

(Continued)

*Primary Examiner* — John Pak
*Assistant Examiner* — Nathan W Schlientz
(74) *Attorney, Agent, or Firm* — Neal, Gerber & Eisenberg LLP

(57) ABSTRACT

An alcoholic foam composition, which can be dispensed as a foam via a pump-foam system contains a) at least 52 to ≤99 wt % of an alcohol or mixture of alcohols, b) a surfactant or a surfactant mixture, c) at least one polyalkylene glycol, d) optionally, at least one foam stabilizer, e) optionally, at least one member selected from the group consisting of cosmetic auxiliaries, adjuvants, active ingredients, and mixtures thereof, and f) optionally water. The surface tension of component b) lies in the range of ±15 dyn/cm of the surface tension of component a) or corresponds to the surface tension of component a), and the sum of components a) to f) is 100 wt % relative to the total quantity of the foam composition.

19 Claims, No Drawings

(56) References Cited

OTHER PUBLICATIONS

Declaration of Amanda J. Copeland and Annexes submitted in the Opposition to European Patent No. 1 811 013 B1.
Submission by Deb Worldwide Healthcare, Inc. in the Opposition to European Patent No. 1 811 013 B1 (including Exhibit E).
Reply dated Dec. 30, 2011 to the European Patent Office Communication dated Jun. 20, 2011 by 3M regarding 06 77 2279.3 including an Amended set of claims (marked-up version and clean copy) and Acknowledgment of receipt.
Examiner's Answer mailed Feb. 9, 2012 to Appeal Brief filed Jul. 18, 2011 for U.S. Appl. No. 11/369,381.
Request for Oral Hearing filed Feb. 8, 2012 in U.S. Appl. No. 12/179,410.
Amendment and Response dated Feb. 12, 2007 in U.S. Appl. No. 11/340,778.
Amendment and Response dated Sep. 11, 2008 in U.S. Appl. No. 11/340,778.
Preliminary Amendment dated Aug. 22, 2006 for U.S. Appl. No. 11/507,626.
Office Action dated Mar. 25, 2011 for U.S. Appl. No. 12/624,073.
Office Action dated Mar. 16, 2009 for U.S. Appl. No. 11/312,559.
Office Action dated Dec. 4, 2008 for U.S. Appl. No. 11/312,559.
Office Action dated Feb. 22, 2007 for U.S. Appl. No. 11/312,559.
Office Action dated Feb. 15, 2011 for U.S. Appl. No. 11/806,767.
Office Action dated Oct. 21, 2011 for U.S. Appl. No. 11/806,767.
Degussa: Goldschmidt Personal Care, Catalogue of Products, p. 30, product ABIL B 8832, Oct. 2004.
Office Action dated Apr. 11, 2011 for U.S. Appl. No. 11/806,767.
Office Action dated Apr. 15, 2011 for U.S. Appl. No. 10/591,243.
Office Action Interview Summary dated Oct. 21, 2011 for U.S. Appl. No. 11/520,819.
Office Action dated Oct. 21, 2011 for U.S. Appl. No. 11/520,819.
Office Action dated Apr. 13, 2011 for U.S. Appl. No. 11/520,819.
Office Action dated Mar. 28, 2012 in U.S. Appl. No. 13/095,698.
Amendment dated Jun. 28, 2012 in U.S. Appl. No. 13/095,698.
Office Action dated Feb. 7, 2013 for Korean Patent Application No. 2007-7022867.
Amendment and Response submitted Feb. 17, 2013 for Japanese Patent Application No. 2008-500017.
Examination Report dated Feb. 26, 2013 from the German Patent Office.
Office Action dated Oct. 10, 2012 from the Chinese Intellectual Property Office.
Response dated Feb. 21, 2013 for Canadian Application No. 2,589,502.
Response dated Apr. 23, 2013 for Canadian Application No. 2,589,502.
Supplementary European Search Report dated Apr. 8, 2013.
Deb Reply, dated Feb. 27, 2013, to Appeal in Opposition to EP1811013.
3M Reply dated Mar. 4, 2013, to Appeal in Opposition to EP1811013.
Gojo Evidence in Opposition to Australian Patent No. 2006252070, dated May 27, 2013.
Marly Skin downloaded from http://www.marley-skin.com/pages/deutsch/produkt.html, dated Sep. 26, 2003.
Patterson, Prevention of sodium lauryl sulfate irritant contact dermatitis by Pro-Q aerosol foam skin protectant, Journal of the American Academy of Dermatology, May, 1999, vol. 40, No. 5, Part 1, pp. 783-785.
Letter dated Dec. 21, 2012 enclosing Statement of Grounds of Opposition in the matter of Australian Patent Application No. 2011224144.
Argument and Amendment regarding Korean Application No. 10-2007-7022867, together with claims, dated Jun. 7, 2013.
Decision of Rejection for Chinese Patent Application No. 200680015637.1 dated Jun. 2013.
Canadian Translation Bureau web page www.btb.termiumplus.gc.ca for CAS No. 125997-17-3, dated May 16, 2013.
Dow Corning Corporation Material Safety Data Sheet for SylGard 309 Silicone Surfactant, revised May 6, 2009.

\* cited by examiner

ALCOHOLIC PUMP FOAM

BACKGROUND OF THE INVENTION

1. Field of the Invention

The present invention relates to alcoholic foam compositions.

2. Discussion of the Background

Disinfectants are used to combat pathogenic microorganisms such as bacteria, viruses, spores, fungi, etc. The use of disinfectants is unavoidable in many regions or the use is expressly required by the legislators in many countries.

Disinfectants are usually classified according to their area of application and, depending on intended use, a distinction is made between antiseptics for wound, skin, stools and sputum disinfection as well as instruments disinfection, laundry and surface disinfectants, and especially also skin and hand disinfectants.

The area of application of the aforesaid disinfectants is medically indicated and they are used for prevention of infections in hospitals, doctors' and dentists' offices, in public areas such as schools, kindergartens, nursing institutions, retirement homes, sanatoriums, etc., and also in sports facilities and other places in which infections can be transmitted. Besides the use of disinfectants in the food industry and pharmaceutical industry, they are in general use not only at the workplace or in the home, but also in service industries such as laundries and kitchens, where the products are delivered directly to patients or consumers.

Demonstration of the effectiveness of such disinfecting agents for one or more of the aforesaid areas of applications is achieved by thorough testing of these agents on the basis of standardized test methods, such as the guidelines of the German Association for Hygiene and Microbiology (DGHM) in Germany or the guidelines of the French Association for Standardization (AFNOR) in France. Examples of further standards are listed below:

| | |
|---|---|
| DIN EN 1040 | Chemical disinfectants and antiseptics (basic test) |
| DIN EN 1276 | Chemical disinfectants and antiseptics Bactericidal action in the fields of foods, industry, home and public institutions |
| DIN EN 1499 | Disinfecting hand washing |
| DIN EN 1500 | Hygienic hand disinfection |
| DIN EN 12054 | Chemical disinfectants and antiseptics Products for hygienic and surgical hand disinfection and hand washing - bactericidal effect |
| DIN EN 12791 | Surgical hand disinfectants |
| AFNOR T 72 300 | Bactericidal effectiveness of antiseptics and disinfectants that are employed as liquid mixed in water |
| AFNOR T 72 170 | Bactericidal effectiveness in the presence of interfering substances |
| NF EN 1040 | Bactericidal effectiveness of antiseptics and chemical disinfectants |
| NF EN 1275 | Fungicidal effectiveness of antiseptics and chemical disinfectants |

In the capacity of pharmaceuticals, antiseptics are further subject to legally governed approval and registration procedures.

For example, as can be seen from German Patent DE 4328828 A, various methods are available for achieving hand disinfection. Explicitly mentioned therein are the alcoholic hand disinfection methods that are standard in Germany as well as the scrub methods of hand disinfection. Products intended for hand disinfection among other purposes must satisfy at least the minimum requirements indicated in the aforesaid standards if they are to be certified as conforming with those standards and included as preparations in the disinfection list of the DGHM.

Commercially available disinfectants, especially skin and hand disinfectants, are usually composed of alcohol or mixtures of alcohols, optionally of active ingredients, which remain on the skin after evaporation of the alcohol components and which can be, for example, nonvolatile antimicrobial substances and/or common skin-care substances, and possibly other auxiliaries. If the alcohol component is used alone as the antimicrobial agent, the alcohol concentration in the product is to be chosen such that a disinfectant effect is assured even after evaporation of part of the alcohol. In this connection, it is known that this is the case for ethanolic compositions having an alcohol concentration of at least 52 wt %.

To address the disadvantages of alcoholic disinfectant solutions applied for skin and hand disinfection, thickeners have been added to such disinfectant solutions in order to increase the viscosity of these agents. Disadvantages include especially the difficulty of dosing due to the fact that the needed quantity of disinfectant often cannot be distributed uniformly over the skin or the hands and that aqueous alcohol solutions drip very easily from the hands. An example for added thickeners is found in European Patent EP 0604848 B, wherein the subject matter is a fast-drying disinfectant composition. As thickener there is described a combination of carboxyvinyl polymers and hydroxypropylmethylcellulose, wherein the total weight of the two components in the disinfectant composition is not greater than 3 wt %.

Also known are antimicrobial alcoholic gel compositions for skin and hand disinfection containing moisturizers and skin-care substances, as described in, for example, U.S. Pat. No. 4,956,170. In these compositions, cross-linked partly neutralized or neutralized acrylic acid polymers are used as thickeners. The antibacterial agent used in these compositions is 60 to 75 wt % of alcohol such as ethanol, isopropyl alcohol or mixtures thereof. Regarding the emollients contained in these gel compositions, especially petrolatum and other mineral-oil products that can be used in cosmetic preparations, as well as further hydrophobic constituents that can be used safely not only in cosmetics but also in disinfectants, it has been found that the use of such constituents in alcoholic gel compositions having high alcohol concentrations is highly detrimental to the stability of such gels, because the gels lose their viscosity and therefore their stability in the course of time during storage, and the compositions deliquesce. In general, it has been found that the gel stability suffers with increasing alcohol concentration, especially at alcohol concentrations higher than 60 wt %.

Such high alcohol concentrations, especially in gel compositions containing alcohol as the sole active component, are unavoidable, however, in order that such agents can also be certified as disinfectants for hand disinfection.

German Patent DE 10132382 discloses a simple, economic production method for the production of stable disinfectant hand-care and skin-care gels having high alcohol concentration, permitting the production of disinfectant hand-care gels that contain care components, that satisfy the standards

| | |
|---|---|
| DIN EN 1499 | Disinfecting hand washing |
| DIN EN 1500 | Hygienic hand disinfection | among others directly without further additional antimicrobial adjuvants, and that also have a hepatitis B activity. Although it has been shown that the application of a disinfectant agent in gel form is to be preferred to the application of a disinfectant agent in liquid form, especially as regards its drying-out tendency, such disinfectant alcoholic gel compositions nevertheless have the disadvantage that they must lose their gel structure upon being applied on the skin, in order to ensure uniform wetting of the skin areas and thus a safe disinfectant action.

Also known are alcoholic cleaning foam compositions, which are dispensed by commercially available pump-foam systems, which are to be found mainly in sanitary units of hospitals, doctors' and dentists' offices, schools, kindergartens and nursing institutions, such as old-age homes, sanatoriums, etc. The alcohol concentration of such foam compositions is only around 40 wt %, however, because the instability of the foams increases at higher alcohol concentrations. This can also be regarded as the reason why the advantageous form of application by means of foam, which is even more manageable than alcoholic gels, has not yet been considered for disinfectants, especially not for skin and hand disinfection, because of the low alcohol concentration of the products that have been commercially available heretofore.

SUMMARY OF THE INVENTION

It is an object of the present invention to provide an alcoholic foam composition that can be dispensed as pump foam, particularly via standard pump-foam systems, to the consumer for disinfection purposes, preferably for skin and hand disinfection.

It is another object of the present invention to provide an alcoholic foam that is stabilized in such a way that alcoholic foam having an alcohol concentration of at least 52 wt %, especially greater than 60 wt % of alcohol can be dispensed in order to ensure safe disinfection, especially skin and hand disinfection.

This and other objects have been achieved by the present invention the first embodiment of which includes an alcoholic foam composition, comprising:
 a) at least 52 to ≤99 wt %, relative to the total quantity of the foam composition, of an alcohol or mixture of alcohols,
 b) a surfactant or a surfactant mixture,
 c) at least one polyalkylene glycol,
 d) optionally, at least one foam stabilizer,
 e) optionally, at least one member selected from the group consisting of cosmetic auxiliaries, adjuvants, active ingredients, and mixtures thereof, and
 f) optionally water,
wherein the surface tension of component b) lies in the range of ±15 dyn/cm of the surface tension of component a) or corresponds to the surface tension of component a), and
wherein the sum of components a) to f) is 100 wt % relative to the total quantity of the foam composition.

DETAILED DESCRIPTION OF THE INVENTION

The present invention provides an alcoholic foam composition for disinfection, especially a pump-foam formulation, which contains the components
 a) at least 52 to ≤99 wt %, relative to the total quantity of the foam composition, of an alcohol or mixture of alcohols,
 b) a surfactant or a surfactant mixture,
 c) at least one polyalkylene glycol,
 d) optionally, at least one foam stabilizer,
 e) optionally, at least one member selected from the group consisting of cosmetic auxiliaries, adjuvants, active ingredients, and mixtures thereof, and
 f) optionally water,
wherein the surface tension of component b) is in the range of ±15 dyn/cm of the surface tension of component a) or corresponds to the surface tension of component a), and the sum of components a) to f) is 100 wt % relative to the total quantity of the foam composition. In other words, the surface tension of component b) is in the range of not less than about 15 dyn/cm below the surface tension of component a) and not more than about 15 dyn/cm above the surface tension of component a).

It was completely surprising that, such alcoholic foam compositions, which preferably are suitable for skin and hand disinfection and which contain at least 52 wt % relative to the total quantity of the foam composition, can be dispensed as foam via standard pump-foam systems, without suffering spontaneous foam breaking because of the high alcohol concentration in the composition. In particular, it would have been expected of such high alcohol concentrations that the alcohol components of such foam compositions would act merely as a solvent at an alcohol concentration of higher than 50 wt %, whereby the surface-active effects of the surfactants and accordingly their foaming ability also would be lowered. Such effects were not observed, however. To the contrary, it was found that stable voluminous foams for disinfection purposes could be produced with the foam compositions according to the present invention in standard pump-foam systems.

According to the present invention, the surface tension of component b) preferably lies in the range of ≥20 to ≤40 dyn/cm. The surface tension of component b) includes all values and subvalues therebetween, especially including 22, 24, 26, 28, 30, 32, 34, 36 and 38 dyn/cm.

Preferably, the alcoholic foam composition contains, as component a), alcohols of the general formula

R—OH in which R denotes an aliphatic straight-chain or branched hydrocarbon group that has 1 to 8 carbon atoms and that can be contained alone or in mixtures in the foam according to the present invention.

Examples of such alcohols are methanol, ethanol, 1-propanol, 2-propanol, 1-butanol, isobutyl alcohol, tert-butyl alcohol, the amyl alcohols, 1-, 2-, 3-pentanol or neopentyl alcohol as well as 1-hexanol, ethanol being particularly preferred as component a).

Preferably, the foam composition contains at least 52 to 99 wt %, preferably 55 to 96 wt % and especially more than 65 wt % of ethanol. The amount of ethanol includes all values and subvalues therebetween, especially including 55, 60, 65, 70, 75, 80, 85, 90 and 95 wt %. As regards the disinfectant action, it is particularly advantageous for the alcoholic foams according to the present invention to contain more than 80 wt % of alcohol.

As component b), the foam compositions according to the present invention can contain respectively a surfactant or surfactant mixture, with the proviso that the surface tension of the :surfactant or of the surfactant mixture contained in the foam composition lies within the range of ±15 dyn/cm of the surface tension of component a), meaning the alcohol component, or corresponds to the surface tension of component a).

Every surfactant or surfactant mixture that satisfies the foregoing proviso is suitable as component b) of the foam compositions. The total quantity of the surfactant or surfactant mixture is 0.5 to 20, preferably 1 to 10 and particularly preferably 2 to 5 wt % relative to the total quantity of the foam composition. The amount of surfactant or surfactant mixture includes all values and subvalues therebetween, especially including 1, 2, 4, 6, 8, 10, 12, 14, 16, and 18 wt %.

Such surfactants are, among other substances, silicone compounds, such as dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers [INCI(CFTA): dimethicone copolyol], which are available from the company named Goldschmidt AG of Essen under the trade name ABIL®, especially polysiloxane-polyether copolymers of the B 88 product family, such as ABM® B 8843, ABIL® B 8851, ABIL® B 8852, ABIL® B 8863, ABIL® B 88183 and ABIL® B 88184. Particularly preferably, the foam compositions according to the present invention contain, as component b), polysiloxane-polyether copolymers available under the trade name ABIL® B 8832. (bis-PEG/PPG-20/20 dimethicone).

As further suitable surfactants or surfactant mixtures there can be mentioned the group of fluoro surfactants, which can be present as component b) in the foams, either alone or as mixture of various fluoro surfactants, especially also as mixtures with polysiloxanepolyether copolymers. Such suitable surfactants are, for example, tetraalkylammonium perfluoroalkylsulfonates, preferably the tetraethylammonium perfluorooctanesulfonate that is commercially available under the trade name FLUORTENSIDE FT-248.

Furthermore, the foam compositions contain, as component c), at least one polyalkylene glycol, which can be present preferably in proportions of 0.01 to 3, especially 0.01 to 0.2 and particularly preferably 0.05 to 0.2 wt % relative to the total quantity of the foam composition. The amount of polyalkylene glycol includes all values and subvalues therebetween, especially including 0.05, 0.1, 0.5, 1, 1.5, 2, and 2.5 wt %. Preferred polyalkylene glycols according to the present invention are in particular polyethylene oxide homopolymers with a molecular weight of 100,000 to 8,000,000, which are available as commercial products on the market under the trademark Polyox®, such as Polyox® WSR N-10, Polyox® WSR N-80 (PEG-5M), Polyox® WSR N-750 (PEG-7M), Polyox® WSR N-3000 (PEG-14M), Polyox® WSR N-3333, Polyox® WSR-205 (PEG-14M), Polyox® WSR-1105, Polyox® WSR N-12K, Polyox® WSR N-60K (PEG-45M) and Polyox® WSR-301.

The foam compositions contain optionally at least one foam stabilizer, which is present as component d) in the foam in a proportion of 0.01 to 20 wt %, preferably 0.5 to 3 wt % relative to the total quantity of the foam composition. The amount of foam stabilizer includes all values and subvalues therebetween, especially including 0.05, 0.1, 0.5, 1, 2, 4, 6, 8, 10, 12, 14, 16 and 18 wt %. Examples of suitable foam stabilizers are polysaccharides, especially xanthan gum, guar-guar, agar-agar, alginates and tyloses, cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose. Preferred according to the present invention are alkylcelluloses, especially methylcellulose and ethylcellulose that are commercially available under the trade names METHOCEL® and ETHOCEL®.

Besides water, the alcoholic foams according to the present invention can if necessary, contain auxiliaries, adjuvants and/or active ingredients, such as dyes, solubilizers, complexing agents, sequestering agents, light-protecting filters or perfumes and scents, pH regulators, stabilizers, preferably cetearyl alcohol and/or hydrogenated castor oils, such as trihydroxystearin, preservatives, antioxidants and/or oil-based or water-based care components as component e), especially in standard proportions of preferably 0.05 to 5 wt % relative to the total weight of the foams. The amount of additional components includes all values and subvalues therebetween, especially including 0.05, 0.1, 0.5, 1, 1.5, 2, 2.5, 3, 3.5, 4 and 4.5 wt %. These optional constituents of component e) can normally be present in proportions of 0 to 5 wt % relative to the total weight of the foam, but the person skilled in the art will choose the weight proportion of component e) such that no impairment of foam formation occurs.

In a preferred embodiment of the present invention, the foams contain 55 to 96 wt % of ethanol, 1 to 10 wt % of bis-PEG/PPG-20/20 dimethicone as silicone surfactant, 0.0 to 3 wt % of ethylcellulose polymer as stabilizer in combination with a PEG polymer, selected from PEG 7M to PEG 45M, preferably 0.05 to 2 wt %, whereby very effectively disinfecting foams with excellent stability are obtained in standard pump-foam systems. These amounts are given based on the total weight of the foam composition. The amount of ethanol includes all values and subvalues therebetween, especially including 60, 65, 70, 75, 80, 85 and 90 wt %. The amount of bis-PEG/PPG-20/20 dimethicone includes all values and subvalues therebetween, especially including 0.1, 0.5, 1, 2, 3, 4, 5, 6, 7, 8 and 9 wt %. The amount of ethylcellulose polymer includes all values and subvalues therebetween, especially including 0.1, 0.5, 1, 1.5, 2 and 2.5 wt %. The amount of PEG polymer includes all values and subvalues therebetween, especially including 0.1, 0.5, 1, and 1.5 wt %.

The alcoholic foams according to the present invention can be used particularly advantageously as disinfectants, for example as antiseptics for wound, skin, stools and sputum disinfection as well as instrument disinfection, as laundry and surface disinfectants and, particularly preferably according to the present invention, as skin and hand disinfectants.

The possible optional addition of nonvolatile antimicrobial substances in the foams is used in particular to intensify the disinfecting properties of the alcohol component. Of course, this depends on the area of application for which the foams are intended.

Antimicrobial substances can be present if necessary and can be used in the foams preferably alone or as combinations of a plurality of disinfectant active ingredients. Preferred are invert soaps, such as cationic surfactants, quaternary ammonium compounds, including benzalkonium chlorides or benzethonium chloride, biguanide compounds, such as chlorhexidine salts, phenol compounds, cresols, per compounds, iodine compounds, such as polyvidone iodine, organic acids, etc.

Nevertheless, the addition of such antimicrobial active ingredients may not be not necessary, since the foams have such a high alcohol concentration that the alcohol component functions as the disinfectant active ingredient on its own.

According to the present invention, care and/or moisturizing active ingredients, which can be contained optionally in the foams, especially for use of the foams as skin and hand disinfectants, are active ingredients that remain on the skin after evaporation of the alcohol component of the foam, for example standard skin-care substances such as dexpanthenol, glycerin, 1,2-propanediol, sorbitol, 1,3-butylene glycol, polyethylene glycol and other polyalcohols, hyaluronic acids, urea, chamomile extracts, alkoxylated cetyl alcohols and/or nonvolatile antimicrobial substances.

Since, during use as skin and hand disinfectants, the high alcohol proportion in the foams causes drying out of the treated skin areas during application, the use of at least one skin-care substance and/or one moisturizer is actually indispensable in daily practice with regard to frequent application of such disinfectants.

Also advantageous for the use of the foams for skin and hand disinfection is a constituent of natural plant tannins, such as ladies' mantle (*Alchemilla xanthochlora*, Rosaceae), tormentil rootstock (*Potentilla erecta*, Rosaceae), oak bark (*Quercus petraea* and *Quercus robur*, Fagaceae), ratanhia root (*Krameria lappacea* syn. *K. triandra*, Krameriaceae), witch hazel leaves (*Hamamelis virginiana*, Hamamelidaceae) and bilberries (*Vaccinium myrtillus*, Ericaceae) and natural synthetic tannins, such as Na bichlorophenylsulfamine, preferably in a proportion of 0.01 to 5 wt % of active substance relative to the total quantity of the foams. Of those, *Hamamelis virginiana* is particularly preferred as tannin. The amount of tannin includes all values and subvalues therebetween, especially including 0.05, 0.1, 0.5, 1, 1.5, 2, 2.5, 3, 3.5, 4 and 4.5 wt %.

Despite their high alcohol concentration, the foams are characterized by very good stability, and so stable disinfectant foams, especially for skin and hand disinfection, are made available by the present invention. Even without further additional antimicrobial adjuvants, these foams satisfy the standards

| DIN EN 1499 | Disinfecting hand washing |
| --- | --- |
| DIN EN 1500 | Hygienic hand disinfection | among others, and in addition have hepatitis B activity. The latter effect especially is particularly advantageous, since the hepatitis B virus, just as the HIV virus that is responsible for the spread of AIDS (acquired immune deficiency syndrome), is communicable but is more stable and more infectious than the HIV virus. Thus, all precautions against transmission of hepatitis B are also preventive against the HIV virus (see Deutsches Arzteblatt 84, No. 18, p. B 874 of 30 Apr. 1987).

Since the foams according to the present invention can have alcohol concentrations of >70 vol % or 60 wt % relative to the total quantity of the foam, they also have virus activity against "naked" or nonenveloped viruses, such as polioviruses and adenoviruses, and so such alcoholic foams are of particular interest as a form of application, especially for skin disinfection.

It is also advantageous that the foams according to the present invention can be dispensed in particular as pump foams via standard pump-foam systems to the consumers for disinfection purposes, preferably for skin and hand disinfection, especially because such pump foams can usually be manufactured inexpensively and simply as aerosol-base foams. Examples include the commercially available pump-foam systems of companies such as Airspray (Netherlands), Keltec (Netherlands), Ophardt (Germany), Brightwell (United Kingdom) and Supermatic (Switzerland).

The foam compositions of the present invention can be obtained by mixing components a) to c) and optionally d), e) and/or f).

Foam compositions preferred according to the present invention (all data in wt % relative to the total quantity of the foam composition):

| | Example | | | | |
| --- | --- | --- | --- | --- | --- |
| | A | B | C | D | E |
| Alcohol or alcohol mixture | 55.0 | 60.0 | 70.0 | 80.0 | 90.0 |
| Polyethylene glycol homopolymer | 0.1 | 0.1 | 0.1 | 0.1 | 0.05 |
| Stabilizer | 0.2 | 0.2 | 0.2 | 0.2 | 0.1 |
| Surfactant or surfactant mixture | 3.0 | 3.0 | 4.0 | 4.0 | 3.0 |
| Water | 41.7 | 36.7 | 25.7 | 15.7 | 6.85 |

Foam compositions preferred according to the present invention for skin and hand disinfection (all data in wt % relative to the total quantity of the foam composition):

| | Example | | |
| --- | --- | --- | --- |
| | 1 | 2 | 3 |
| Ethanol | 55.0 | 80.0 | 90.0 |
| PEG-14M | 0.1 | 0.1 | 0.05 |
| Ethylcellulose | 0.2 | 0.2 | 0.1 |
| Bis-PEG/PPG-20/20 dimethicone | 3.0 | 4.0 | 3.0 |
| Demineralized water | 41.7 | 15.7 | 6.85 |

German patent application 10 2004 062 775.4 filed, Dec, 21, 2004, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. An alcoholic foamable composition, comprising:
a) at least 52 to ≤99 wt %, relative to the total quantity of the foamable composition, of an alcohol or mixture of alcohols,
b) 0.5 to 20 wt. %, relative to the total quantity of the foamable composition, of at least one silicone surfactant, wherein said at least one silicone surfactant is not fluorinated, and said at least one silicone surfactant is selected from polysiloxane-polyether copolymers, and
c) 0.01 to 3 wt. %, relative to the total quantity of the foamable composition, of at least one polyalkylene glycol, wherein at least one of said polyalkylene glycol is a polyethylene oxide homopolymer,
d) optionally, 0.01 to 20 wt. %, relative to the total quantity of the foamable composition, of at least one foam stabilizer,
e) optionally, at least one member selected from the group consisting of cosmetic auxiliaries, adjuvants, active ingredients, and mixtures thereof, and
f) optionally water,
wherein the sum of components a) to f) is 100 wt % relative to the total quantity of the foamable composition, and wherein said alcoholic foamable composition is in the form of a pump-foam formulation before it is foamed, said pump-foam formulation being capable of forming a stabilized pump-foam.

2. The alcoholic foamable composition according to claim 1, wherein component a) comprises an alcohol or a mixture of alcohols of formula R—OH wherein R denotes an aliphatic straight-chain or branched hydrocarbon group having 1 to 8 carbon atoms.

3. The alcoholic foamable composition according to claim 1, wherein component a) comprises at least one member selected from the group consisting of methanol, ethanol, 1-propanol, 2-propanol, 1-butanol, isobutyl alcohol, tert-butyl alcohol, the amyl alcohols, 1-petanol, 2-pentanol, 3-pentanol, neopentyl alcohol, 1-hexanol and mixtures thereof.

4. The alcoholic foamable composition according to claim 1, wherein at least 52 to ≤99 wt %, relative to the total quantity of the foamable composition, of ethanol is contained in the foamable composition alone or as part of component a).

5. The alcoholic foamable composition according to claim 1, wherein at least 60 wt %, relative to the total quantity of the foamable composition, of ethanol is contained in the foamable composition as component a).

6. The alcoholic foamable composition according to claim 1, wherein one or more of the polyethylene oxide homopolymers are selected from the group consisting of PEG-5M, PEG-7M, PEG-14M, PEG-23M, PEG-45M, and PEG-90M.

7. The alcoholic foamable composition according to claim 1, wherein the at least one polyalkylene glycol is selected from polyethylene oxide homopolymers having a molecular weight of from 100,000 to 8,000,000.

8. The alcoholic foamable composition according to claim 1, wherein 0.01 to 10 wt %, relative to the total quantity of the foamable composition, of at least one foam stabilizer is contained in the foamable composition as component d).

9. The alcoholic foamable composition according to claim 1, comprising an alkylcellulose as component d).

10. The alcoholic foamable composition according to claim 1, comprising: 55 to 96 wt % of ethanol, 1 to 10 wt % of the polysiloxane-polyether copolymer surfactant, 0.0 to 3 wt % of ethylcellulose polymer, and 0.05 to 2 wt % PEG polymer selected from the group consisting of PEG 7M to PEG 45M and mixtures thereof.

11. A disinfectant, comprising: the alcoholic foamable composition according to claim 1.

12. An antiseptic for wound, skin, stools and sputum disinfection or instrument disinfection, comprising: the alcoholic foamable composition according to claim 1.

13. A laundry and surface disinfectant, comprising: the alcoholic foamable composition according to claim 1.

14. A skin and hand disinfectant, comprising: the alcoholic foamable composition according to claim 1.

15. A method of disinfecting skin with a stabilized pump foam said method comprising: applying a stabilized pump foam to the skin of a consumer, wherein stabilized pump foam is formed from the alcoholic foamable composition according to claim 1.

16. The method of claim 15, wherein the stabilized pump foam is applied to a hand of the consumer.

17. The method of claim 15, wherein component a) of the foamable composition is ethanol at a concentration of greater than 60 wt %, relative to the total quantity of the foamable composition.

18. A method of dispensing a stabilized pump foam, said method comprising: dispensing a stabilized pump foam from a pump-foam system, wherein the stabilized pump foam is formed from the alcoholic foamable composition according to claim 1.

19. A pump-foam system for dispensing a stabilized pump foam, said pump-foam system comprising: the alcoholic foamable composition according to claim 1 to be dispensed via the pump-foam system.

* * * * *